(12) United States Patent
Hutchins et al.

(10) Patent No.: US 7,087,425 B2
(45) Date of Patent: Aug. 8, 2006

(54) METHOD OF PURIFYING OOCYSTS USING ENZYMATIC DIGESTION OF FECAL DEBRIS

(75) Inventors: James E. Hutchins, Durham, NC (US); Robert C. Tuttle, Columbus, OH (US)

(73) Assignee: Embrex, Inc., Durham, NC (US)

( * ) Notice: Subject to any disclaimer, the term of this patent is extended or adjusted under 35 U.S.C. 154(b) by 0 days.

(21) Appl. No.: 11/092,064

(22) Filed: Mar. 29, 2005

(65) Prior Publication Data

US 2005/0244946 A1 Nov. 3, 2005

Related U.S. Application Data

(60) Provisional application No. 60/558,348, filed on Mar. 31, 2004.

(51) Int. Cl.
*C12P 1/10* (2006.01)
*A61K 39/12* (2006.01)

(52) U.S. Cl. .................. 435/258.4; 424/171.1; 435/264; 435/268

(58) Field of Classification Search ............. 435/258.4, 435/264, 268; 424/271.1
See application file for complete search history.

(56) References Cited

U.S. PATENT DOCUMENTS

| | | |
|---|---|---|
| 3,147,186 A | 9/1964 | Edgar |
| 4,544,548 A | 10/1985 | Davis et al. |
| 4,863,731 A | 9/1989 | Davis et al. |
| 5,055,292 A | 10/1991 | McDonald et al. |
| 5,932,225 A * | 8/1999 | Wallach et al. ........ 424/267.1 |
| 5,958,758 A | 9/1999 | Miller et al. |
| 6,083,395 A | 7/2000 | Katsura et al. |
| 6,333,062 B1 | 12/2001 | Fontana et al. |
| RE38,047 E | 3/2003 | Fodge et al. |
| 6,585,895 B1 | 7/2003 | Smith et al. |
| 6,908,620 B1 * | 6/2005 | McDougald et al. ..... 424/267.1 |
| 2003/0143717 A1 * | 7/2003 | Hutchins et al. ........ 435/258.1 |
| 2003/0175311 A1 * | 9/2003 | Binger et al. ............ 424/271.1 |

FOREIGN PATENT DOCUMENTS

| | | |
|---|---|---|
| WO | WO 91/04673 A1 | 4/1991 |
| WO | WO 2000/26341 | 5/2000 |
| WO | WO 2000/50072 | 8/2000 |
| WO | WO 2002/37961 | 5/2002 |
| WO | WO 2003/020917 | 3/2003 |
| WO | WO 03/072044 A2 | 9/2003 |

OTHER PUBLICATIONS

Ermatova et al "Amylolytic activity of the mucous membranes of the intestines of chickens during experimental infection with *Eimeria mitis coccidia*" Abs 1978:149314 CAPLUS DN 88:149314 Uzbekskii Biol. Zhurnal (1977) (6) 31-32.*
International Search Report and the Written Opinion of the International Searching Authority for International patent application No. PCT/US2005/010930 mailed on Aug. 1, 2005.
Watkins, et al., "The Effect of In Ovo Oocyst or Sporocyst Inoculation on Response to Subsequent Coccidial Challenge" *Poultry Science* 74(10): 1597-1602 (1995).
Ryley et al. Methods in coccidiosis research: separation of oocysts from faeces. *Parasitology*, 73, pp. 311-326. (1976).
Sriroth et al. Processing of cassava waste for improved biomass utiltization. *Bioresource Technology*, 71, pp. 63-69. (2000).
Parmar et al. Enzyme treatment to reduce solids and improve settling of sewage sludge. *Journal of Industrial Microbiology & Biotechnology*, 26, pp. 383-386. (2001).

* cited by examiner

*Primary Examiner*—Herbert J. Lilling
(74) *Attorney, Agent, or Firm*—Myers Bigel Sibley & Sajovec, P.A.

(57) ABSTRACT

The invention provides methods and compositions for purifying protozoan oocysts. In particular embodiments, the oocysts are *Eimeria* oocysts. The methods comprise contacting a composition comprising fecal material and protozoan oocysts with polysaccharidase under conditions sufficient to reduce the amount of fecal material in the composition.

38 Claims, 1 Drawing Sheet

FIGURE 1

METHOD OF PURIFYING OOCYSTS USING ENZYMATIC DIGESTION OF FECAL DEBRIS

RELATED APPLICATION INFORMATION

This application claims the benefit of U.S. Provisional Application No. 60/558,348 filed Mar. 31, 2004, which is incorporated by reference herein in its entirety.

FIELD OF THE INVENTION

The present invention provides methods and compositions for the purification of protozoan oocysts; in particular, the present invention provides methods and compositions for the purification of *Eimeria* oocysts that can be used to produce vaccines.

BACKGROUND OF THE INVENTION

Coccidiosis of poultry is a disease caused by protozoan parasites of the genus *Eimeria*. Oocysts of *Eimeria* species are ubiquitous in the environment and persist for many months in poultry litter. Ingestion of oocysts leads to infection of the various regions of the intestinal tract in a species-specific manner. The organism proliferates in the intestine over a period of several days, resulting in the excretion of the next generation of oocysts in the feces. Multiple cycles of infection lead to immunity, and when the infection is presented to a flock early and in a uniform dosage among the flock, the immunity developed over several cycles of exposure can be quite robust.

In contrast, when birds are not presented with the infection in a uniform manner, situations may arise in which naive birds are subject to sudden, massive infection, leading to poor performance in terms of feed conversion and weight gain, and a high risk of secondary infections. Currently, the most common method used for control of coccidiosis in the poultry industry is not vaccination, but rather the administration of anticoccidial drugs in the feed. The low rate of vaccination is often attributed to uncertainty in the uniformity in dosing via the feed or water at the growout facility or by spray cabinet vaccination at the hatchery, which are the traditional routes and times of administration. There is increasing interest in improving the uniformity of delivery during administration at the hatchery.

Recently, in ovo vaccination techniques have been found applicable to administration of a live oocyst-based coccidiosis vaccine (see, e.g., U.S. Pat. No. 6,500,438; U.S. Pat. No. 6,495,146; and U.S. Pat. No. 6,627,205; all to Pfizer, Inc.). The in ovo route of administration provides a convenient method of delivering a uniform dose of vaccine to each embryo while it is still in the egg. Delivery of avian vaccines in ovo is currently practiced for approximately 85% of the 9 billion broiler birds produced in the United States each year and in a growing percentage of the 21 billion broiler birds produced outside of the United States each year (see, e.g., U.S. Pat. No. 4,458,630; to the United States government). Therefore, the potential market for a live, in ovo-delivered coccidiosis vaccine is considerably larger than the current market for post hatch-delivered coccidiosis vaccines.

Oocysts for use in a live coccidiosis vaccine are derived from feces, which are initially heavily laden with contaminating microorganisms. Typically, regulatory agencies require that in ovo-delivered vaccines be shown to be essentially free of contaminating microorganisms. To ensure that bioburden levels are fully minimized in the final product, it is beneficial to use compositions and methodologies that effectively control the level of contaminating microorganisms at each stage of the oocyst production process. Reduction in extraneous solids may increase the efficiency of bioburden reduction methodologies.

Accordingly, there is a need in the art for improved methods of purifying protozoan oocysts, especially for use in vaccine manufacture.

SUMMARY OF THE INVENTION

The present invention relates to improved methods and compositions for purifying protozoan oocysts (e.g., *Eimeria* oocysts), for example, for use in the manufacture of vaccines. With particular respect to poultry vaccines, the invention is suitable for producing vaccines for post hatch or in ovo use. Likewise, the vaccine can be used in the broiler, laying, breeder, turkey, hobbyist and/or domesticated bird industries.

The present invention is based, in part, on the discovery that fecal material containing oocysts can be enzymatically digested by polysaccharidase without unduly impacting oocyst viability and/or recovery. Thus, the invention provides improved methods for reducing fecal material in a composition comprising oocysts by digesting the fecal material with polysaccharidase. The invention also provides methods of purifying oocysts from a composition comprising fecal material by a process that comprises digesting fecal material in the composition with polysaccharidase. The polysaccharidase acts to cleave the solid, insoluble plant debris into soluble sub-components, which can be removed. For example, the soluble products of enzyme digestion can be removed by separating and concentrating the oocysts via techniques such as centrifugation or tangential flow filtration.

The methods and compositions of the invention are advantageous for commercial oocyst production processes (e.g., for vaccines) by reducing the fecal load and facilitating the use of a smaller process scale. Minimization of extraneous fecal debris in the composition is beneficial for the control of contaminating microorganisms and, if desired, the production of a sterile end-product. Further, enzymatic digestion can substantially reduce the amount of solids in the composition, thereby resulting in a proportionately reduced scale of operation for all downstream processes. The reduction in process scale can make the process more efficient and economical.

Enzyme digestion can be incorporated into a larger purification scheme and can be used in conjunction with, or as a substitute for, current techniques for purifying oocysts (e.g., sieving, flotation, centrifugation, etc.). If flotation processes are replaced by enzyme digestion, the advantages include (1) eliminating or reducing salts, which are corrosive to equipment, from the purification process; and/or (2) improved robustness of the process. If the enzyme digestion is used prior to a flotation step, the benefits can include a reduction in the volume of the flotation solution, which is generally directly proportional to the starting volume of the fecal matter.

Accordingly, as a first aspect, the invention provides a method of purifying oocysts (e.g., viable oocysts) from a composition comprising fecal material, the method comprising contacting the composition with polysaccharidase under conditions sufficient to reduce the amount of fecal material in the composition. In particular embodiments, the polysaccharidase comprises, consists essentially of, or consists of cellulase. In other embodiments, the polysaccharidase comprises, consists essentially of, or consists of cellulase and pectinase. In still further representative embodiments, the polysaccharidase comprises, consists essentially of, or consists of cellulase, pectinase and amylase.

As a further aspect, the invention provides methods of purifying *Eimeria* oocysts (e.g., viable *Eimeria* oocysts) from a composition comprising fecal material, the method comprising contacting the composition with polysaccharidase comprising cellulase under conditions sufficient to reduce the amount of fecal material in the composition.

The invention also provides methods of purifying *Eimeria* oocysts (e.g., viable *Eimeria* oocysts) for use in producing a vaccine, the method comprising the method comprising contacting the composition with polysaccharidase comprising cellulase under conditions sufficient to reduce the amount of fecal material in the composition.

As yet another aspect, the invention provides a composition comprising polysaccharidase for use in purifying protozoan oocysts (for example, to manufacture vaccines) using the methods of the invention.

These and other aspects of the invention are set forth in more detail in the description of the invention below.

DETAILED DESCRIPTION OF THE INVENTION

The present invention will now be described with reference to preferred embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

The present invention is suitable for purifying oocysts for both medical and veterinary uses. The terms "animal" and "animal subjects" include but are not limited to mammalian and/or avian subjects.

Suitable mammalian subjects include but are not limited to human subjects and non-human primate subjects such as simian, porcine, bovine (e.g., cattle), caprine, equine, feline, ovine, canine, murine (e.g., mouse, rat) and lagomorph subjects.

The terms "avian" and "avian subjects" (i.e., "bird" and "bird subjects"), as used herein, are intended to include males and females of any avian species, but are primarily intended to encompass poultry that are commercially raised for eggs, meat or as pets. Accordingly, the terms "avian" and "avian subject" are particularly intended to encompass but not be limited to chickens, turkeys, ducks, geese, quail, pheasant, parakeets, parrots, cockatoo, cockatiel, ostrich, emu and the like. In particular embodiments, the avian subject is a chicken or a turkey subject. In other embodiments, the avian subject is a chicken. As used herein, an "avian" or "avian subject" can refer to an avian embryo in ovo or an avian post hatch.

The present invention relates generally to methods and compositions for the purification protozoan oocysts. Such methods and compositions find use, for example, in methods of manufacturing vaccines. Additionally, the methods can be used to purify oocysts which have been genetically modified, for example, for recombinant protein production. Many protozoa form a life stage designated as an "oocyst." The invention can be practiced to purify oocysts from any species of protozoa, including but not limited to *Eimeria, Cryptosporidium, Toxoplasma, Plasmodia* and *Isospora*. In embodiments of the invention, the methods and compositions of the invention are used to purify *Eimeria* oocysts.

The terms "protozoa," "oocyst," "sporocyst," "sporozoite" and "merozoite" have their accepted meaning in the art. Unless indicated otherwise, these terms are intended to refer to live (i.e., viable) protozoa, oocysts, sporocysts, sporozoites and merozoites, including attenuated forms, although those skilled in the art will appreciate that vaccines can be formulated using killed protozoa, oocysts, sporocysts, sporozoites and merozoites. It is understood by those skilled in the art that killed vaccines are usually prepared by first purifying the live organism. Also encompassed are genetically modified protozoa, oocysts, sporocysts, sporozoites and merozoites. Oocysts can be sporulated or non-sporulated.

The term "*Eimeria*" indicates one or more species of the genus *Eimeria*. The term "*Eimeria*" includes but is not limited to strains or species of *Eimeria* that infect birds (e.g., chicken, turkey) or mammalian (e.g., cattle, sheep or rabbit) species. Such *Eimeria* species include those that are found in chickens, including *E. tenella, E. acervulina, E. maxima, E. necatrix, E. mitis, E. praecox, E. mivati* and *E. brunetti*; and also those that are found in turkeys, including *E. meleagrimitis, E. adenoeides, E. gallopavonis, E. dispersa, E. innocua,* and *E. subrotunda,* and those that infect cattle such as *E. bovis* and *E. zuernii; Eimeria* species that infect sheep such as *E. ahsata, E. bakuensis, E. crandallis, E. faurei, E. granulosa, E. intricata, E. marsica, E. ovinoidalis, E. pallida, E. parva, E. weybridgensis;* and *Eimeria* species that infect rabbits including *E. intestinalis, E. vejdovskyi, E. piriformis, E. coecicola, E. irresidua, E. flavescens, E. exigua, E. magna, E. perforans, E. media,* and *E. stiedai*. In addition, the term "*Eimeria*" includes all strains of the foregoing species of *Eimeria*, including but not limited to wildtype strains, precocious or otherwise selected strains, attenuated strains, and oocysts that have been attenuated, e.g., by irradiation, chemical treatment and the like. Further, the term "*Eimeria*" also includes any newly-discovered strains or species of *Eimeria*. Finally, the term "*Eimeria*" encompasses live and killed *Eimeria*, although live *Eimeria* are intended unless indicated otherwise.

Viability can be assessed, for example, by determining the infectivity of the oocysts in a host. In particular embodiments, "viable" oocysts purified according to the methods of the invention have at least about 60%, 70%, 80%, 90%, 95%, 99% of the infectivity of oocysts that have not been subjected to enzyme treatment according to the present invention.

Compositions comprising *Eimeria* oocysts find use in methods of immunizing birds against coccidiosis. Methods of vaccinating birds against coccidiosis are known in the art, and include in ovo (e.g., U.S. Pat. No. 6,500,438; U.S. Pat. No. 6,495,146; and U.S. Pat. No. 6,627,205; Pfizer Inc.) and post hatch (e.g., U.S. Pat. No. 3,147,186 to Auburn Research Foundation; U.S. Pat. No. 5,055,292 and U.S. Pat. No. 4,438,097, both to National Research Development Corporation) vaccination methods.

Those skilled in the art will appreciate that oocysts can be further processed to release other life stages (e.g., sporozoites or sporocysts) for use in the final vaccine composition, or to produce extracts or proteins for vaccination purposes.

The term "protozoa" includes wildtype strains, precocious or otherwise selected strains, attenuated strains, and oocysts that have been attenuated, e.g., by irradiation, chemical treatment and the like. Further, the term "protozoa" also includes any newly-discovered strains or species of protozoans. Finally, the term "protozoa" covers both live and killed protozoa, although live protozoa are intended unless indicated otherwise.

The terms "produce," "producing" or "production" of oocysts, and the like generally refer to the process of harvesting oocysts from an animal and purifying the oocysts from the fecal material.

Unless indicated otherwise, the terms "purify(ies)," "purification," "purifying," and "purified" as used herein with respect to preparations of oocysts refer to the separation from, or removal of, fecal debris and other unwanted material from preparations containing the oocysts. These terms are intended to indicate that the degree of isolation or separation of the oocysts from other material present in the feces is enhanced, not that absolutely all (or even most) extraneous material is removed from the oocyst preparations. Likewise, the oocyst preparation can contain some degree of microbial contamination, as long as the final preparation is suitable for its intended use (e.g., as a post-hatch vaccine). In particular embodiments, vaccines intended for in ovo administration to birds are essentially free of detectable contamination by unwanted microorganisms (i.e., other than the protozoan oocysts of interest), in particular, contaminating microorganisms that are pathogenic (i.e., cause significant illness or mortality) to the embryo.

Depending upon context, a "purification" process can refer to the entire process of purifying oocysts from feces to produce a preparation suitable for vaccination purposes. Alternatively, a "purification" process can refer to any subset of steps, or even a single step, within the entire purification scheme.

The present invention provides methods and compositions for purifying oocysts (e.g., *Eimeria* oocysts). The inventive digestion methods can be combined with one or more other purification steps as part of a purification scheme. For example, the methods of the invention can be used in conjunction with other methods known in the art.

Methods of producing oocysts, such as *Eimeria* oocysts, are known in the art (see, e.g., U.S. Pat. No. 3,147,186 to Auburn Research Foundation; U.S. Pat. No. 4,544,548 to Internationale Octrooi Maatschappij "Octropa" B.V.; U.S. Pat. No. 4,863,731 to Unilever Patent Holdings; international patent publications WO 00/50072 to Pfizer, Inc.; WO 03/020917 to Embrex, Inc.; and WO 02/37961 to Novus International, Inc.; Hammond et al., (1944) *Amer. J. Vet. Res.* 5:70; Hill et al., (1961) *J. Parasit.* 47:357; Jackson, (1964) *Parasitology* 54:87; Lotze et al., (1961) *J. Parasit.* 47:588; Schmatz et al., (1984) *J. Protozool.* 31:181; Whitlock, (1959) *Aust. Vet. J.* 35:310).

As used herein, if one step or process is "carried out before" or "carried out after" or equivalent language another step or process, it is meant that the first step or process occurs prior to or after, respectively, the second step in the purification scheme and does not exclude the possibility of intermediate steps.

The terms "microbial contamination," "contamination by microorganisms," and like terms are intended to indicate the presence of detectable and unwanted viable microorganisms including but not limited to bacteria, molds, fungi, yeast and viruses (i.e., microorganisms other than the protozoan oocysts of interest). In particular embodiments, the oocyst preparation is essentially free of detectable microbial contamination, meaning that no significant level of microbial contamination is detected in the preparation, or the oocyst preparation is free of any detectable microbial contamination. Methods of detecting microorganisms are known in the art and depend on the class of microorganism being detected.

By "sanitizing" or "sanitization" or "sanitized" (and like terms) it is intended that there is a reduction in the microbial contamination (i.e., viable contaminating microorganisms, as defined above) in the oocyst preparation. It is not necessary that the oocyst preparation contain absolutely no microbial contamination, as long as the final preparation is suitable for its intended use (e.g., as a vaccine). In the case of compositions intended for in ovo administration to birds, the preparation will generally be essentially free of detectable microbial contamination (i.e., no significant levels of contaminating microorganisms are detected) or free of any detectable microbial contamination, i.e., is axenic.

The abbreviation "v/v" refers to "volume/volume." The abbreviation "w/v" refers to "weight/volume."

Individual aspects of the present invention are described in more detail below.

Purifying Protozoan Oocysts by Enzyme Digestion of Fecal Debris.

The present inventors have made the discovery that enzyme digestion with polysaccharidase can be used to reduce fecal debris without unduly reducing viability and/or recovery of protozoan oocysts. The polysaccharidase acts to degrade insoluble plant material to a soluble (e.g., in aqueous solution) form that can readily be removed from the oocysts. Thus, the invention provides methods of purifying oocysts from a composition comprising fecal material, where the methods comprise contacting the composition with polysaccharidase under conditions sufficient to reduce the amount of fecal material (i.e., solubilize and thus render easily removable some or all of the solid fecal material) in the composition. In particular embodiments, the oocysts are viable oocysts.

The methods of the invention can be practiced with any composition comprising fecal material and oocysts. To illustrate, oocysts can be collected from feces, cecal cores, intestinal linings or other tissues, and the like from infected animals. For commercial purposes, the oocysts are typically collected from the feces of infected animals.

The polysaccharidase according to the present invention can comprise one or more polysaccharide degrading enzymes. When two or more polysaccharide degrading enzymes are used in the methods of the invention, the enzymes can be used concurrently or sequentially in any order. Polysaccharidases are known in the art and include but are not limited to cellulase, pectinase, amylase, xylanase, arabinase, α-galactosidase, hemi-cellulase, β-glucanase, β-glucosidase, and amyloglucosidase.

In one representative embodiment of the invention, the polysaccharidase comprises, consists essentially of, or consists of cellulase. By "consists essentially of" cellulase, it is meant that the polysaccharidase contains only insignificant levels of a polysaccharidase other than cellulase.

In other representative embodiments, the composition is contacted with a cellulase and a pectinase. In other exemplary embodiments, the composition is subjected to digestion by a cellulase, a pectinase and an amylase. In one such embodiment, the composition is first digested with the cellulase and the pectinase, and is then subject to digestion with the amylase (e.g., after the enzymatic degradation with the cellulase and pectinase are complete or substantially complete, e.g., at least 70%, 80% or 90% complete).

The specific reaction conditions for the enzymatic digestion can be selected and optimized to achieve any desired endpoint(s) such as degree of purity, recovery of oocysts, viability of oocysts, process scale, time efficiency, cost efficiency, compatibility with other steps in the process, compatibility with equipment, and the like.

The amount of enzyme added to the composition is selected to achieve the desired level of purification without adversely affecting recovery and/or viability of the oocysts. Those skilled in the art will appreciate that the time period required for completion of the enzyme digestion is dependent on temperature and enzyme concentration as well as the particular enzyme used. Thus, with lower enzyme concentrations, a longer reaction time and/or higher reaction temperature is typically used to obtain the same extent of digestion.

In particular embodiments, each enzyme is present at a concentration of at least about $0.25 \times 10^3$ units/liter, about $0.5 \times 10^3$ units/liter, about $1 \times 10^3$ units/liter, about $2 \times 10^3$ units/liter, about $5 \times 10^3$ units/liter, about $1 \times 10^4$ units/liter, about $2 \times 10^4$ units/liter, about $4 \times 10^4$ units/liter, about $5 \times 10^4$ units/liter, about $1 \times 10^5$ units/liter, about $2 \times 10^5$ units/liter or about $3 \times 10^5$ units/liter and less than about $2 \times 10^4$ units/liter, about $3 \times 10^4$ units/liter, about $5 \times 10^4$ units/liter, about $8 \times 10^4$ units/liter, about $10 \times 10^4$ units/liter, about $12 \times 10^4$ units/liter, about $15 \times 10^4$ units/liter, about $20 \times 10^4$ units/liter, about $25 \times 10^4$ units/liter, about $30 \times 10^4$ units/liter, about $40 \times 10^4$ units/liter, about $50 \times 10^4$ units/liter, about $10 \times 10^5$ units/liter, about $15 \times 10^5$ units/liter, about $20 \times 10^5$ units/liter, about $35 \times 10^5$ units/liter, about $50 \times 10^5$ units/liter, about $10 \times 10^6$ units/liter, about $20 \times 10^6$ units/liter, about $25 \times 10^6$ units/liter, or about $30 \times 10^6$ or more, with any combination of upper and lower limits.

With respect to cellulase, in illustrative embodiments, cellulase is present in an amount of about $0.5 \times 10^4$ to $35 \times 10^5$ units per liter, about $1 \times 10^4$ to $15 \times 10^5$ units/liter, about $2 \times 10^4$ to $50 \times 10^4$ units/liter, about $3 \times 10^4$ to $30 \times 10^4$ units units/liter, about $4 \times 10^4$ to $25 \times 10^4$ units/liter, or about $8 \times 10^4$ to $20 \times 10^4$ units/liter or more.

For pectinase, in representative embodiments, pectinase is present in an amount of about $5 \times 10^4$ to $20 \times 10^6$ units/liter, about $1 \times 10^5$ to $10 \times 10^6$ units/liter, about $2 \times 10^5$ to $5 \times 10^6$ units/liter, or about $3 \times 10^5$ to $2.5 \times 10^6$ units/liter or more.

For amylase, in representative embodiments, amylase is present in an amount of about $0.25 \times 10^3$ to $15 \times 10^4$ units/liter, about $0.5 \times 10^3$ to $8 \times 10^4$ units/liter, about $1 \times 10^3$ to $5 \times 10^4$ units/liter, or about $2 \times 10^3$ to $3 \times 10^4$ units/liter or more.

The duration of the enzyme digestion is selected to achieve the desired reduction in fecal debris without adversely affecting recovery and/or viability of the oocysts. As discussed above, the rate of the enzyme reaction generally depends on reaction temperature, enzyme concentration and the particular polysaccharidase used. In particular embodiments, the digestion reaction is carried out for at least about 30 minutes, 45 minutes, 1 hour, 2 hours or 3 hours and for as long as about 3, 4, 6, 8, 10, 12, 15, 18, 20, 24, 30 or 36 hours or longer, with any combination of upper and lower limits. Illustrative time ranges for performing the enzyme digestion are from about 30 minutes to 24 hours, from about 1 to 20 hours, from about 1 to 15 hours, from about 2 to 10 hours, from about 2 to 8 hours, and from about 2 to 5 hours. In some instances, the enzyme digestion is carried out for a longer time period than is necessary to complete the digestion reaction. For example, it may be convenient to carry out the digestion overnight, even though the reaction is complete in a shorter time period.

The enzyme digestion process is typically carried out at a temperature(s) that achieves the desired reaction rate (i.e., process time) but that does not adversely affect recovery and/or viability of the oocysts. In general, the temperature is usually less than about 31° C. or 32° C. In embodiments of the invention, the temperature is at least about 12, 15, 18, 20, 21, 22 or 24° C. and is less than about 26, 27, 28, 29 or 30° C., with any combination of upper and lower limits. Illustrative temperatures for the enzyme digestion are in the range of about 15° C. to 30° C., about 18° C. to 29° C., and about 21° C. to 27° C.

Similarly, the pH of the reaction can be routinely selected to achieve the desired level of enzyme activity and purification of the oocysts. In exemplary embodiments, digestion with cellulase and/or pectinase is carried out at a pH in the range of about pH 1 to pH 7.5, about pH 2 to pH 6.5, about pH 3 to pH 6, or about pH 4 to pH 5.5 or 6. In the case of amylase, the reaction is generally carried out at from about pH 4 to pH 7.5, depending in part on the source of the amylase (e.g., from bacteria or fungi). In particular embodiments, the reaction is carried out in a range from about pH 4.5 to pH 7, about pH 6 to pH 8 or about pH 6.5 to pH 7.5.

If more than one enzyme is used for digestion, the pH of the solution can be adjusted for each enzyme reaction. In exemplary methods, the composition is first digested with cellulase and/or pectinase at a pH in the range of about pH 3 to pH 6 or about pH 4 to pH 5.5 or 6. The pH of the solution is then adjusted to about pH 4 to pH 7.5 or about pH 6.5 to pH 7.5, for example, by addition of base or by exchange with a solution in the desired pH range (e.g., pelleting by centrifugation and resuspension in the new solution) for the amylase digestion.

By carrying out the reaction within a temperature or pH "range," it is meant that the reaction can be performed at one or more than one temperatures or pH within the indicated temperature or pH range, respectively.

After the desired level of enzymatic digestion has been achieved, the enzyme(s) can optionally be removed (e.g., by separating the oocysts from the liquid material by standard techniques such as centrifugation or tangential flow filtration) or inactivated (e.g., by changing temperature and/or pH and/or by chemical inactivation). Thus, in particular embodiments, the method further comprises removing the enzyme from contact with the oocysts, and optionally collecting the oocysts (for example, by centrifugation, flotation or tangential flow filtration) for the next step in the purification scheme, for sanitization, or for an end use such as vaccine manufacture).

An exemplary enzyme digestion method according to the present invention is set forth below. According to this embodiment, the composition comprises *Eimeria* oocysts. The composition is digested with cellulase, and optionally pectinase, for about 2 to 18 hours, at a temperature in the range of about 21° C. to 27° C., and a pH in the range of about pH 4 to pH 6. The concentration of cellulase is in the range of about $8 \times 10^4$ to $20 \times 10^4$ units/liter and, if present, the concentration of pectinase is in the range of about $1 \times 10^5$ to $10 \times 10^6$ units/liter.

The enzyme digestion methods of the invention can be used alone or can be incorporated into a larger oocyst purification scheme. Methods of producing oocysts are known in the art and include methods of producing *Eimeria* oocysts as described by U.S. Pat. No. 3,147,186 to Auburn Research Foundation; U.S. Pat. No. 4,544,548 to Internationale Octrooi Maatschappij "Octropa" B.V.; U.S. Pat. No. 4,863,731 to Unilever Patent Holdings; international patent publications WO 00/50072 to Pfizer, Inc.; WO 03/020917 to Embrex, Inc.; and WO 02/37961 to Novus International, Inc.; Hammond et al., (1944) *Amer. J. Vet. Res.* 5:70; Hill et al., (1961) *J. Parasit.* 47:357; Jackson, (1964) *Parasitology* 54:87; Lotze et al., (1961) *J. Parasit.* 47:588; Schmatz et al., (1984) *J. Protozool.* 31:181; Whitlock, (1959) *Aust. Vet. J.* 35:310 (the disclosures of which are incorporated by reference herein in their entirety).

In general, these methods involve infecting an animal with the protozoan of interest, collecting feces that contain oocysts from the infected animal, purifying the oocysts from the fecal material through a series of separation procedures such as sieving, centrifugation, filtration and/or density flotation, sporulating the oocysts, optional additional separation steps, and, if desired, sanitizing the sporulated oocysts to inactivate contaminating microorganisms. Different oocyst preparations (e.g., from different species or strains) can then be combined to form a final product, for example, a vaccine against multiple protozoan (e.g., *Eimeria*) species.

The enzyme digestion can be carried out at any point within the oocyst purification process. The enzymatic digestion can be performed during or upon completion of collection of the feces, prior to upstream purification processes such as sieving. In other representative embodiments, the enzyme digestion process is carried out after the upstream purification steps, such as sieving or centrifugation. In general, it can be advantageous to use the enzyme digestion process prior to downstream purification steps such as flotation to reduce process scale. In other embodiments, the enzyme digestion is performed prior to, or instead of, downstream purification steps, such as flotation. Further, sporulation of the oocysts can occur prior to, concurrently with, or after the enzyme digestion. In some embodiments, the oocysts are concentrated before or after sporulation either by pelleting via centrifugation or by removal of liquid by techniques such as tangential flow filtration. The enzymatic digestion process can be incorporated either before or after such a concentration step. In one illustrative embodiment of the invention, the oocysts in the fecal composition are subjected to upstream purification steps (e.g., centrifugation and/or sieving) and then sporulation. According to this embodiment, the enzyme digestion is carried out at a point after the sporulation step and prior to (or instead of) the downstream purification steps, such as density flotation.

In particular embodiments, the purification process further comprises a density flotation step, for example, flotation in a salt (e.g., magnesium sulfate) or glycerol (e.g., glycerol-arginine) solution. Salt and nonionic density flotation solutions and density flotation methods using salt and nonionic solutions are described in international patent publications WO 00/50072 (Pfizer, Inc.) and WO 03/020917 (Embrex, Inc.), which are incorporated by reference herein in their entireties. In representative embodiments, the density flotation process is carried out after the enzyme digestion process.

Methods of performing density flotation of oocysts are known in the art. In particular embodiments, the density flotation comprises: suspending a preparation containing oocysts in a composition comprising a high density liquid to form a suspension under conditions sufficient to result in flotation of the oocysts, and recovering the oocysts from the suspension. Generally, the material containing the oocysts is admixed with the flotation solution, and the solution is allowed to separate, with the oocysts remaining in the supernatant fraction and the fecal debris forming a pellet. Centrifugation can be used to facilitate or improve the separation.

The flotation medium can be removed from the oocysts by any suitable method known in the art, including centrifugation/wash steps, dialysis and filtration (e.g., tangential flow filtration).

If desired, the purified oocysts can be sanitized to produce a sterile solution. A sanitization step is an optional step that is typically employed in methods of producing oocysts for in ovo avian vaccines and is sometimes used for post hatch avian vaccines as well. As known in the art, oocysts for use in vaccine preparations are conventionally sanitized using sodium hypochlorite solutions. Other methods of sanitizing oocysts are described in WO 03/020917 (Embrex, Inc.); the disclosure of which is incorporated herein by reference in its entirety.

In embodiments of the invention, the enzyme digestion (and, optionally, other purification steps) is carried out in an anti-microbial solution. The action of the polysaccharidase in releasing simple carbohydrates can potentially promote the rapid growth of contaminating microorganisms. Examples of suitable anti-microbial solutions are disclosed in international patent publication WO 03/020917 (Embrex, Inc.); the disclosure of which is incorporated herein by reference in its entirety.

In particular embodiments, the composition comprising the fecal material and the oocysts is contacted with other enzymes such as lipase and/or protease in addition to polysaccharidase (e.g., concurrently or sequentially in any order).

The inventors have further found that the efficiency of enzymatic digestion of fecal debris can be influenced by the diet fed to the animals from which the fecal material is collected. In particular embodiments, the animals are fed a diet having a large mean particle size during and/or prior to the oocyst collection period. Exemplary large particle diets contain whole grains such as barley, corn (e.g., cracked corn), wheat, oats, millet and/or sorghum. For example, feeding a diet containing barley to birds appears to produce a composition that is more efficiently digested. The barley can be in any form that is suitable for use in a poultry diet, such as steamed-flaked barley. Thus, the methods of the invention can be carried out with fecal material containing oocysts collected from a bird(s) fed a diet containing barley, for example a barley-soy diet. Illustrative diets contain at least about 15%, 20%, 25%, 30%, 35%, 40%, 50%, 60%, 70%, 80%, 90%, 95% or more barley (w/w). Other exemplary diets contain about 15% to 70% (w/w), about 20% to 60% (w/w), about 20% to 50% (w/w), about 25% to 45% (w/w), or about 25% to 40% (w/w) barley. One representative diet contains about 35% (w/w) steamed-flaked barley, about 35% (w/w) high protein soy meal, about 10% (w/w) crimped oats, about 6% (w/w) rice bran and other fats, minerals, vitamins and supplements to support the health of the birds.

Animal diets having a large mean particle size are described in WO 03/020917 (Embrex, Inc.), which is incorporated by reference herein in its entirety.

Methods of feeding enzymes to birds to improve digestibility of polysaccharide-containing feed (see, e.g., U.S. RE38,047; hemicellulase), to enhance growth rate (see, e.g., U.S. Pat. No. 6,333,062; alpha-galactosidase), to treat malabsorption (see, e.g., U.S. WO 91/04673; cellulase or xylanase) and/or pasty vent syndrome are known in the art. Thus, polysaccharidase can be fed to the animals (e.g., birds) from which the fecal material is collected and the oocysts harvested. Multi-enzyme preparations are commercially available, e.g., Natugrain®, Selfeed®, and Hemicell®.

The enzymatic digestion methods of the invention can be carried out to achieve the desired reductions in fecal material, for example, by at least about 30%, 40%, 50%, 60%, 70%, 80%, 85%, 90%, 95% (v/v), (w/w) or (w/v) or higher.

Further, in particular embodiments, the recovery of oocysts (optionally, viable oocysts) from the enzyme digestion process is at least about 60%, 70%, 80%, 85%, 90%, 95%, 98% (v/v), (w/w) or (w/v) or higher. Methods of determining oocyst viability are known in the art, for example by assessing infectivity of the oocysts (see, e.g., Example 7).

Immunogenic Compositions.

Immunogenic compositions produced using the methods of the present invention can be administered to an animal subject to vaccinate against a protozoan disease. An immunogenic composition (e.g., a vaccine) containing oocysts produced using the methods of the present invention can be administered to elicit an immune response. Typically, the immunogenic composition comprises an immunogenic amount of oocysts as disclosed herein in combination with a pharmaceutically-acceptable carrier. An "immunogenic amount" is an amount of the oocysts that is sufficient to initiate or evoke an immune response in the subject to which the immunogenic composition is administered. As understood by those skilled in the art, the immunogenic composition can be formulated with live, attenuated and/or killed organisms. This approach is also applicable to other parasitic life stages, such as sporozoites or sporocysts.

By "pharmaceutically acceptable" it is meant a material that is not biologically or otherwise undesirable, i.e., the material may be administered to a subject without causing undesirable biological effects. Thus, such a pharmaceutical composition may be used, for example, to prepare compositions for immunization. Pharmaceutically acceptable carriers may contain other compounds including but not limited to stabilizers, salts, buffers, adjuvants and/or preservatives (e.g., antibacterial, antifungal and antiviral agents) as are known in the art. The pharmaceutically acceptable carrier need not be sterile, although it generally will be for in ovo administration to avian embryos.

Any route of administration of the immunogenic composition known in the art can be employed as long as an active immune response (preferably, a protective immune response) against the protozoa is elicited. When the subject is a bird, the immunogenic composition may be administered in ovo or post-hatch. Exemplary routes of administration are post-hatch oral administration or in ovo injection (e.g., into the amnion). In particular embodiments of the invention, in ovo administration using automated injection equipment is employed.

The terms "vaccination" or "immunization" are well-understood in the art. For example, the terms vaccination or immunization can be understood to be a process that results in and/or increases a subject's immune reaction to antigen, and therefore its ability to resist or overcome infection. In ovo methods of vaccinating birds against Eimeria are known in the art (e.g., U.S. Pat. No. 6,500,438; U.S. Pat. No. 6,495,146; and U.S. Pat. No. 6,627,205; Pfizer, Inc.).

The terms "protective immunity" or "protective immune response," as used herein, are intended to mean that the host animal mounts an active immune response to the vaccine, such that upon subsequent exposure or challenge, the animal is able to combat the infection. Thus, a protective immune response will decrease the incidence of morbidity and mortality from subsequent exposure to the pathogen among treated animals. Those skilled in the art will understand that in a commercial animal husbandry setting, the production of a protective immune response can be assessed by evaluating the effects of vaccination on the flock or herd as a whole, e.g., there may still be signs of illness or of morbidity and mortality in a minority of vaccinated animals.

By "active immune response," it is meant any level of protection from subsequent exposure to the protozoa or protozoan antigens that is of some benefit in a population of subjects, whether in the form of decreased mortality, decreased lesions, improved feed conversion ratios, or the reduction of any other detrimental effect of the disease, and the like, regardless of whether the protection is partial or complete. An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection, or as in the present case, by vaccination. Active immunity can be contrasted with passive immunity, which is acquired through the "transfer of preformed substances (antibody, transfer factor, thymic graft, interleukin-2) from an actively immunized host to a non-immune host." Id.

The Examples, which follow, are set forth to illustrate the present invention, and are not to be construed as limiting thereof.

EXAMPLE 1

Enzyme Tests

An initial experiment was performed to test the feasibility of using digestive enzymes to purify Eimeria oocysts. *E. maxima* oocysts were produced in broilers. Feces containing oocysts were collected 5 to 8 days post-inoculation into an antimicrobial solution consisting of 10% citric acid, 0.75 to 3% hydrogen peroxide, and 0.25% propionic acid. Materials were sieved to remove large debris and sporulated in 10% citric acid, 0.75 to 3% hydrogen peroxide, and 0.25% propionic acid with stirring and aeration for at least 48 h. A sample of material was taken after sporulation and subjected to various enzyme treatments (see Table 1). Enzymes (cellulase and amylase) were obtained from two commercial sources (Novozymes and Genencor) for use in this experiment. Enzymes were added at 20% (v/v) to each preparation. The pH of the sample was adjusted to approximately pH 4.5 for cellulase treatment or cellulase+amylase treatment and to pH 7.0 for amylase treatment alone. Materials were incubated for up to 3 days with gentle agitation, and oocyst counts and debris determinations were performed. Oocysts were enumerated by the McMasters' method (Hodgson, J. N., (1970) Coccidiosis: oocysts counting technique for coccidiostat evaluation. *Exper. Parasitol.* 28:99–102). Debris values were determined by centrifuging a representative subsample at 1800×g for 10 min, measuring the volume of pelleted solids and calculating the volume of pelletable solids per volume of sample. Total solids were then determined by multiplying the value for pelletable solids per mL sample by the total sample volume. Results are presented in the Table 1 below.

In this and the following examples, the specific activity of the enzyme preparations received from the manufacturer were as follows: cellulase ($8.4 \times 10^5$ units/liter); pectinase ($2.6 \times 10^7$ units/liter); and amylase ($3 \times 10^5$ units/liter). Materials were diluted on a v/v basis as indicated for each experiment.

debris had been made soluble after 1 day of incubation. Debris reduction did not change much with further incubation. Based on these results, additional studies were performed focusing on cellulase and/or amylase treatment.

EXAMPLE 2

Multi-Enzyme Experiments I: Studies Using Fecal Solids from which Oocysts had been Removed Broiler birds were infected with *E. maxima* oocysts, and the oocyst-containing feces were collected 5 to 8 days post infection. Feces were collected into 10% citric acid, 0.75 to 3% hydrogen peroxide, and 0.25% propionic acid. The suspension was sieved to remove large particles, and oocysts were sporulated for at least 48 h in 10% citric acid, 0.75 to 3% hydrogen peroxide, and 0.25% propionic acid with stirring and aeration. Following sporulation, the suspension was centrifuged to pellet the oocysts and fecal debris, and the supernatant was discarded. The pellet was resuspended in magnesium sulfate flotation solution adjusted to a density of 1.2 g/mL and centrifuged at 1800×g for approximately 10 min. Oocysts, contained in the supernatant, were diluted

TABLE 1

Treatment of Chicken Feces Containing *E. maxima* Sporulated Oocysts with Enzymes.

| Treatment Designation | Enzymes | Source | Days of incubation | Total oocysts | Total Pellet (mL) | Percent debris reduction | Overall Oocyst Yield (%) |
|---|---|---|---|---|---|---|---|
| Control 1 | None | N/A | 1 | 3.75E+06 | 4.100 | 0.00 | 100.0 |
| Control 2 | None | N/A | 2 | 4.19E+06 | 4.500 | −9.76 | 111.7 |
| Control 3 | None | N/A | 3 | 4.40E+06 | 4.000 | 2.44 | 117.3 |
| A1 | Amylases | Novozymes | 1 | ND | 3.800 | −15.85 | ND |
| A2 | Amylases | Novozymes | 2 | ND | 3.400 | −3.66 | ND |
| A3 | Amylases | Novozymes | 3 | 2.42E+06 | 2.500 | 23.78 | 80.7 |
| B1 | Cellulases | Novozymes | 1 | 3.02E+06 | 0.900 | 72.56 | 100.7 |
| B2 | Cellulases | Novozymes | 2 | 2.85E+06 | 0.900 | 72.56 | 95.0 |
| B3 | Cellulases | Novozymes | 3 | 2.70E+06 | 0.800 | 75.61 | 90.0 |
| AB1 | Amylases and cellulases | Novozymes | 1 | 1.63E+06 | 1.000 | 59.35 | 72.4 |
| AB2 | Amylases and cellulases | Novozymes | 2 | 1.78E+06 | 0.900 | 63.41 | 79.1 |
| AB3 | Amylases and cellulases | Novozymes | 3 | 1.55E+06 | 0.900 | 63.41 | 68.9 |
| C1 | Amylases | Genencor | 1 | ND | 3.900 | −18.90 | ND |
| C2 | Amylases | Genencor | 2 | ND | 3.100 | 5.49 | ND |
| C3 | Amylases | Genencor | 3 | 1.75E+06 | 3.000 | 8.54 | 58.3 |
| D1 | Cellulases | Genencor | 1 | ND | 2.900 | 11.59 | ND |
| D2 | Cellulases | Genencor | 2 | ND | 2.200 | 32.93 | ND |
| D3 | Cellulases | Genencor | 3 | 3.05E+06 | 2.700 | 17.68 | 101.7 |
| CD1 | Amylases and cellulases | Genencor | 1 | 2.42E+06 | 1.500 | 39.02 | 107.6 |
| CD2 | Amylases and cellulases | Genencor | 2 | 2.23E+06 | 1.400 | 43.09 | 99.1 |
| CD3 | Amylases and cellulases | Genencor | 3 | 1.47E+06 | 1.200 | 51.22 | 65.3 |

ND: Not determined.

Results.

Control samples appeared normal. The best result was observed with the Novozymes cellulase at 1-day incubation. Essentially quantitative recovery of oocysts was obtained, and the oocysts had a normal appearance. About 73% of the with water and processed further for use in other experiments. The remaining pelleted material, which represented the undigested fecal material from the production birds, was resuspended in 10% citric acid and 0.25% propionic acid. These solids represent the target insoluble residual plant debris from the feces which were to be solubilized via enzymatic digestion. The solids were used in a series of experiments to evaluate various enzymatic digestion conditions. Debris reduction was evaluated as described in Example 1.

Treatment Using Cellulase and Cellulase+Xylanase.

Nine replicate 15 mL pellets were prepared by centrifuging portions of the solids described above. Pellets were washed once with PBS. The suspension was then centrifuged and pellets resuspended in the appropriate treatment solution.

TABLE 2

Cellulase and Xylanase Treatments.

| Treatment # | Description | # Replicates | Starting pellet volume per replicate (mL) |
|---|---|---|---|
| 1 | Buffer control. PBS adjusted to pH 5.0. | 3 | 15 |
| 2 | 20% Cellulase in PBS adjusted to pH 5.0 | 3 | 15 |
| 3 | 20% Cellulase plus xylanase at 17 units per mL in solution | 3 | 15 |

All replicates were incubated at room temperature overnight with gentle agitation. The suspensions were then centrifuged at 3000 rpm for 10 minutes, and the volume of the pelleted solids was measured.

TABLE 3

Results of Multi-Enzyme Experiment I: Enzymatic Treatment of Fecal Solids from which Oocysts had been Removed

| Treatment | Debris (mL pellet) tube 1 | Debris (mL pellet) tube 2 | Debris (mL pellet) tube 3 | Average pellet (mL) | % Pellet reduction step |
|---|---|---|---|---|---|
| 1-Buffer control | 15 | 15 | 15 | 15.00 | 0.0 |
| 2-Cellulase | 4.5 | 5 | 5 | 4.83 | 67.8 |
| 3-Cellulase + xylanase | 4.5 | 5 | 5 | 4.83 | 67.8 |

Results.

The cellulase treatment provided a 67% reduction in debris. The cellulase+xylanase treatment did not appear to offer any advantage over cellulase treatment alone.

An additional experiment was performed using the 3 replicate tubes from Experiment I Treatment 2-Cellulase. Pectinase, amyloglucosidase, or beta-glucosidase was added directly to the cellulase treatment and incubated overnight with gentle agitation.

TABLE 4

Treatment with cellulase followed by pectinase, amyloglucosidase, or beta-glucosidase.

| Treatment | Pellet volume start (mL) | Pellet volume final (mL) | Comments |
|---|---|---|---|
| 2-cellulase; then added pectinase | 4.5 | 4.5 | Clarified supernatant |
| 2-cellulase; then added amyloglucosidase | 5 | 5 | No visible change |

TABLE 4-continued

Treatment with cellulase followed by pectinase, amyloglucosidase, or beta-glucosidase.

| Treatment | Pellet volume start (mL) | Pellet volume final (mL) | Comments |
|---|---|---|---|
| 2-cellulase; then added beta-glucosidase | 5 | 5 | No visible change |

Results.

The cellulase+pectinase treatment yielded a clarified supernatant above the heavier debris pellet. Neither amyloglucosidase nor beta-glucosidase treatment offered any visible advantage over cellulase treatment alone.

EXAMPLE 3

Multi-Enzyme Experiments II: Studies Using Fecal Material Containing *Eimeria* Oocysts Broiler chickens were inoculated with any of *E. acervulina*, *E. maxima*, or *E. tenella* oocysts. Feces containing oocysts were collected during the peak oocyst output period for each species. Feces were collected into an antimicrobial solution consisting of 10% citric acid, approximately 0.75 to 3% hydrogen peroxide, and 0.25% propionic acid. The samples were sieved to remove large debris particles and centrifuged to pellet the debris.

Three replicate samples, each consisting of 5 mL pelleted solids resuspended in PBS pH 5.0 served as controls for each treatment. Three replicate samples per enzyme treatment were prepared. Samples were resuspended in either 20% cellulase solution or 20% cellulase with 4% pectinase in PBS pH 5.0 and incubated at room temperature with gentle agitation for at least 4 h. Oocysts were enumerated in control and treatment samples using the McMasters method, and solids were determined by the methods described in Example 1. Debris reduction and oocyst recovery were calculated relative to control samples.

Preparation of Solids.

Nine replicate ~5-mL pellets were prepared from each sample. Pellets were washed once using PBS. Washed pellets were resuspended in the appropriate enzyme solution for treatments 1–3 as indicated in Table 5 below.

TABLE 5

Treatment using Cellulase or Cellulase + Pectinase.

| Treatment # | Description | # Replicates | Starting pellet volume per replicate (mL) |
|---|---|---|---|
| 1 | Buffer control. PBS adjusted to pH 5.0. | 3 | 5 |
| 2 | 20% Cellulase 1.5 L in PBS adjusted to pH 5.0 | 3 | 5 |
| 3 | 20% Cellulase plus 4% pectinase, pH 5.0 | 3 | 5 |

Procedure.

Upon preparation of treatments 1–3, oocyst enumeration and debris measurement was performed for Treatment 1 Buffer controls. Treatments 2 and 3 were incubated overnight with gentle agitation. Following incubation, oocysts were enumerated and debris determinations performed for Treatments 2 and 3.

Treatments 2-amylase and 3-amylase were then prepared using residual materials from treatments 2 and 3 as indicated in Table 6.

TABLE 6

Treatments using cellulase or cellulase + pectinase followed by amylase.

| Treatment # | Description | # Replicates | Starting pellet volume per replicate (mL) |
|---|---|---|---|
| 2-Amylase | 20% Cellulase; followed by 2% amylase at pH 7 | 3 | 5 |
| 3-Amylase | 20% Cellulase plus 4% pectinase; followed by 2% amylase at pH 7 | 3 | 5 |

Tubes containing the residual material from Treatments 2 and 3 were centrifuged and the pellets washed once with PBS. Washed pellets were resuspended in amylase solution. Following overnight incubation at room temperature with gentle agitation, oocysts were enumerated (Hodgson, J. N., (1970) Coccidiosis: oocysts counting technique for coccidiostat evaluation. *Exper. Parasitol.* 28:99–102) and debris determinations performed for Treatments #2 and 3.

TABLE 7

Results of Enzyme Tests using Chicken Feces containing *E. acervulina* Oocysts.

| Treatment | Average pellet (mL) | % Pellet reduction step | % Pellet reduction total | Average total oocysts | Oocyst recovery step (%) | Oocyst recovery overall (%) |
|---|---|---|---|---|---|---|
| 1-Buffer control | 3.50 | 0 | 0 | 1.29E+07 | 100.0 | 100.0 |
| 2-Cellulase | 1.77 | 50 | 50 | 7.33E+06 | 57.0 | 57.0 |
| 3-Cellulase + pectinase | 1.50 | 57 | 57 | 8.73E+06 | 67.8 | 67.8 |
| 2-Cellulase; followed by amylase | 1.27 | 28 | 64 | 8.75E+06 | 119.3 | 68.0 |
| 3-Cellulase + pectinase; followed by amylase | 0.73 | 51 | 79 | 8.22E+06 | 94.2 | 63.9 |

Results.

The cellulase+pectinase treatment yielded a higher debris reduction than cellulase treatment alone. Amylase treatment yielded better debris reduction when the sample was treated first with cellulase+pectinase. Approximately 79% of the debris was removed using cellulase+pectinase treatment followed by amylase treatment. Overall oocyst recovery varied between 57 and 68% for these treatments. Enzyme treatment provided acceptable oocyst recovery, comparable to or better than the 50 to 90% oocyst recovery typically achieved via standard flotation techniques.

TABLE 8

Results of enzyme tests using chicken feces containing *E. tenella* oocysts.

| Treatment | Average pellet (mL) | % Pellet reduction step | % Pellet reduction total | Average total oocysts | Oocyst recovery step (%) | Oocyst recovery overall (%) |
|---|---|---|---|---|---|---|
| 1-Buffer control | 5.00 | 0 | 0 | 1.82E+07 | 100.0 | 100.0 |
| 2-Cellulase | 3.50 | 30 | 30 | 1.90E+07 | 104.5 | 104.5 |
| 3-Cellulase + pectinase | 2.00 | 60 | 60 | 1.36E+07 | 74.9 | 74.9 |
| 2-Cellulase; followed by amylase | 2.43 | 30 | 51 | 1.46E+07 | 76.9 | 80.3 |
| 3-Cellulase + pectinase; followed by amylase | 1.33 | 33 | 73 | 1.68E+07 | 123.4 | 92.4 |

Results.

Cellulase+pectinase yielded a much higher debris reduction, approximately two-fold that of the cellulase treatment alone. Amylase treatment yielded better debris reduction when the sample was treated first with cellulase+pectinase. Approximately 73% of the debris was removed using cellulase+pectinase treatment followed by amylase treatment. Overall oocyst recovery was essentially quantitative in this set of experiments.

TABLE 9

Results of enzyme tests using chicken feces containing *E. maxima* oocysts

| Treatment | Average pellet (mL) | % Pellet reduction step | % Pellet reduction total | Average total oocysts | Oocyst recovery step (%) | Oocyst recovery overall (%) |
|---|---|---|---|---|---|---|
| 1-Buffer control | 3.93 | 0 | 0 | 1.59E+06 | 100.0 | 100.0 |
| 2-Cellulase | 2.00 | 49 | 49 | 1.85E+06 | 116.6 | 116.6 |
| 3-Cellulase + pectinase | 1.60 | 59 | 59 | 1.44E+06 | 90.8 | 90.8 |
| 2-Cellulase; followed by amylase | 1.73 | 13 | 56 | 1.12E+06 | 60.2 | 70.2 |
| 3-Cellulase + pectinase; followed by amylase | 0.73 | 54 | 81 | 1.15E+06 | 79.8 | 72.5 |

Results.

Cellulase+pectinase yielded a higher debris reduction than cellulase treatment alone. Amylase treatment yielded much better debris reduction (~4× higher) when the sample was treated first with cellulase+pectinase. Approximately 81% of the debris was removed using cellulase+pectinase treatment followed by amylase treatment. Overall oocyst recovery was approximately 70% in this set of experiments.

Overall Conclusions.

Cellulase+pectinase yielded a higher debris reduction than cellulase treatment alone. Amylase treatment yielded much better debris reduction (~5× higher) when the sample was treated first with cellulase+pectinase. Approximately 80% of the debris was removed using cellulase+pectinase treatment followed by amylase treatment. Overall oocyst recovery was approximately 75 to 95% in this set of experiments.

Summary.

Enzymatic digestion using a combination of cellulase and pectinase at pH 5 reduced debris levels after sporulation by approximately 60% for all vaccine strains; oocyst recovery averaged approximately 82%.

Cellulase+pectinase treatment followed by digestion with amylase at pH 7 yielded a total of approximately 80% debris reduction after sporulation; oocyst recovery after amylase treatment averaged 94.4% for the step. Overall oocyst recovery using the sequence of enzyme treatments averaged 76%.

EXAMPLE 4

Debris Digestion Using Cellulase and Pectinase for Three *Eimeria* Species

Broiler chickens were inoculated with any of *E. acervulina*, *E. maxima*, or *E. tenella* oocysts. Feces containing oocysts were collected during the peak oocyst output period for each species. Feces were collected into an antimicrobial solution consisting of 10% citric acid, approximately 0.75 to 3% hydrogen peroxide, and 0.25% propionic acid. The samples were sieved to remove large debris particles and centrifuged to pellet the debris.

Three replicate samples, each consisting of 5 mL pelleted solids resuspended in PBS pH 5.0 served as controls for each treatment. Three replicate samples per enzyme treatment were prepared. Samples were resuspended in either 20% cellulase solution or 20% cellulase with 4% pectinase in PBS pH 5.0 and incubated at room temperature with gentle agitation for at least 4 h. Oocysts were enumerated using standard microscopic techniques in control and treatment samples, and solids were determined by centrifugation of samples and measurement of the pellet volume. Debris reduction and oocyst recovery were calculated relative to control samples. Results are shown in Table 10 below:

TABLE 10

Debris Digestion using Cellulase Alone or in Combination with Pectinase for Three *Eimeria* Species.

| | 20% Cellulase | | 20% Cellulase + 4% Pectinase | |
|---|---|---|---|---|
| Species | % Pellet Reduction | % Oocyst Recovery | % Pellet Reduction | % Oocyst Recovery |
| *E. acervulina* | 50 | 57 | 57 | 68 |
| *E. maxima* | 51 | 112 | 60 | 94 |
| *E. tenella* | 30 | 105 | 60 | 75 |

Results indicate that cellulase in combination with pectinase yielded a higher debris reduction than cellulase treatment alone. Either treatment provided acceptable oocyst recovery, comparable to or better than the 50 to 90% oocyst recovery typically achieved via standard flotation techniques.

EXAMPLE 5

Time Course of Fecal Debris Digestion Using 20% Cellulase and 4% Pectinase

Broiler chickens were inoculated with *E. maxima* oocysts. Feces containing oocysts were collected 5 to 8 days post inoculation. Feces were collected into an antimicrobial solution consisting of 10% citric acid, approximately 0.75 to 3% hydrogen peroxide, and 0.25% propionic acid. The sample was sieved to remove large debris particles and centrifuged to pellet the debris.

Figure 1:
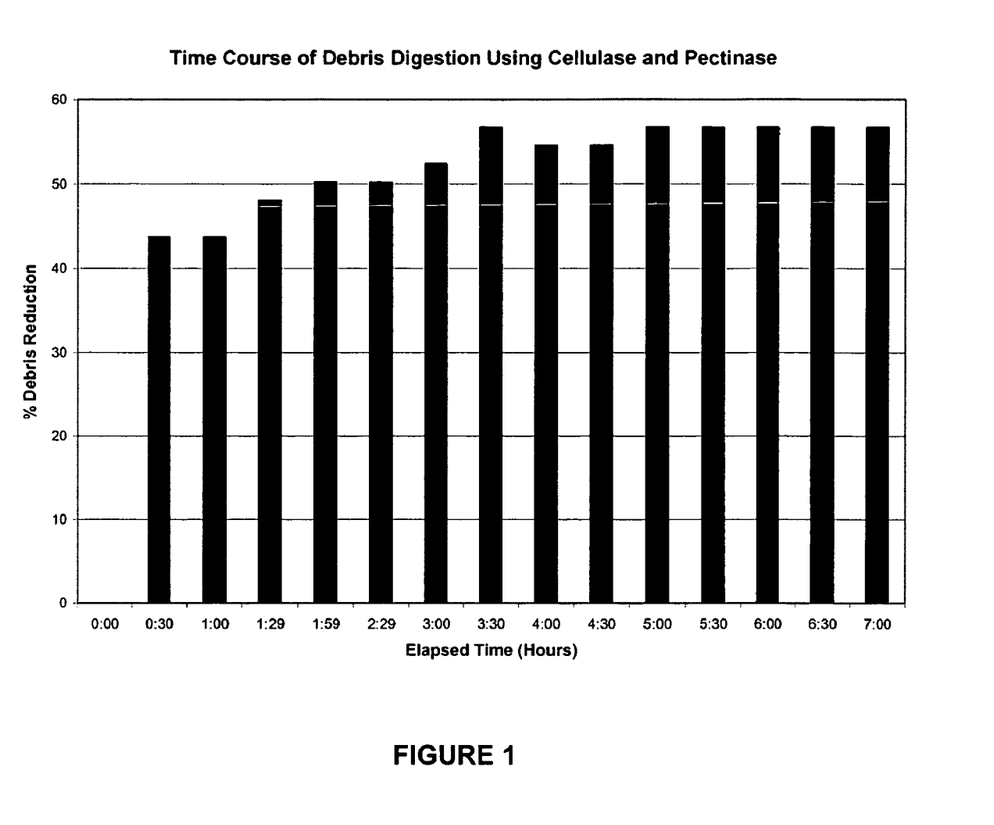
FIG. 1 shows a time course of fecal debris digestion using 20% (v/v) cellulase and 4% (v/v) pectinase.

Twenty replicate 5 mL samples of the pelleted solids were prepared. The pH of the samples was adjusted to approximately pH 5.0. The samples were centrifuged to pellet the solids. Two control samples were resuspended in PBS adjusted to pH 5.0. The two samples were centrifuged to pellet the solids and the volume of the pellets were measured. The remaining 18 samples were resuspended in 20% cellulase plus 4% pectinase in PBS adjusted to pH 5.0. Samples were incubated at room temperature with gentle agitation. At approximately half-hour intervals, one replicate was centrifuged and the volume of the pellet was measured. Percent debris reduction was calculated in relation to the average pellet volume of the two control samples. Results are shown in FIG. 1.

Results indicate that the enzymatic digestion of debris using a combination of cellulase and pectinase was approximately 90% complete in about 1 hour and about 99% complete in 3 to 5 hours. Overall, cellulase and pectinase solubilized approximately 57% of the debris in the sample.

EXAMPLE 6

Use of Enzymes in Feed

The use of enzymes in chicken feed is known to contribute to the overall digestibility of the feed. The possibility that enzymes in the feed would also reduce fecal solid levels upon collection of oocysts was evaluated. A corn/soy diet was tested with and without the presence of supplemental enzymes in the formulation. A combination of three commercial enzyme preparations was included in the enzyme-containing diet (Natugrain®, Selfeed®, and Hemicell®). Broilers were placed at 9 per pen using 5 replicate pens for each of the two diet treatments. Birds were inoculated with *E. maxima* oocysts. Feces containing oocysts were collected days 5 to 8 post inoculation. Feces were collected into an antimicrobial solution consisting of 10% citric acid, approximately 0.75 to 3% hydrogen peroxide, and 0.25% propionic acid. Each replicate sample was adjusted to 8 L total volume, stirred well, and subsampled. Two ~50 mL subsamples were taken from each sample and stored at 4° C. Samples were analyzed for debris content and oocyst concentration. Two replicate 8 L samples were pooled and sieved to remove large debris particles and centrifuged to pellet the debris. Variables assessed in the study included initial debris levels and oocyst output per bird.

Table 11 shows the average pellet material per bird in feces collected 5 to 8 days post inoculation and average oocysts per bird. For those pens where mortality occurred the average number of birds was calculated based upon day of mortality. Treatments were compared using independent sample t-tests and no significant treatment differences were found for either pellet per bird or oocyst output per bird, although pellet per bird was numerically lower with enzymes added to the diet.

No significant differences were found in pellet volume per bird or oocyst output per bird between the experimental diets with vs. without enzymes.

TABLE 11

Comparison of Average Oocysts per Bird and Pellet per Bird for Pens with Different Diets after *E. maxima* Challenge.

| Diet | Statistic | Pellet volume per bird (mL) | Total oocysts per bird |
|---|---|---|---|
| Corn/soy | Mean | 140.6 | $3.23 \times 10^7$ |
| | Standard deviation | 13.5 | $5.64 \times 10^6$ |
| | N | 5 | 5 |
| Corn/soy with enzymes | Mean | 127.7 | $3.16 \times 10^7$ |
| | Standard deviation | 17.4 | $5.46 \times 10^6$ |
| | N | 5 | 5 |

Main effect of diet not significant (p > .05).

Samples of the fecal material derived from the corn/soy diet with and without enzymes were sieved and the results compared. For each treatment, two replicate samples representing a total of 18 birds were pooled and sieved sequentially through 18, 60, and 230 mesh screens. Volumes were recorded and representative subsamples were taken at each stage of sieving. Samples were analyzed for debris content and oocyst concentration. Oocyst recovery and debris reduction through the sieving process were calculated.

TABLE 12

Analysis of Sieving Results using the Corn/Soy Diet.

| Description | Volume (L) | Total oocysts | Total Pellet (mL) | Percent debris reduction (step) | Percent debris reduction (overall) | % Total Oocyst Recovery (Step) | Overall Yield (%) |
|---|---|---|---|---|---|---|---|
| Starting material | 16 | 5.84E+08 | 3200 | 0.00 | 0.00 | 100.00 | 100.0 |
| Post 18 mesh | 21 | 6.15E+08 | 2100 | 34.38 | 34.38 | 105.36 | 105.4 |
| Post 60 mesh | 23 | 5.36E+08 | 1380 | 34.29 | 56.88 | 87.10 | 91.8 |
| Post 230 mesh | 25.5 | 4.59E+08 | 1020 | 26.09 | 68.13 | 85.65 | 78.6 |

TABLE 13

Analysis of Sieving Results using the Corn/Soy + Enzymes Diet.

| Description | Volume (L) | Total oocysts | Total Pellet (mL) | Percent debris reduction (step) | Percent debris reduction (overall) | % Total Oocyst Recovery (Step) | Overall Yield (%) |
|---|---|---|---|---|---|---|---|
| Starting material | 16 | 6.93E+08 | 2560 | 0.00 | 0.00 | 100.00 | 100.0 |
| Post 18 mesh | 19 | 6.27E+08 | 1710 | 33.20 | 33.20 | 90.50 | 90.5 |
| Post 60 mesh | 22 | 5.59E+08 | 1320 | 22.81 | 48.44 | 89.12 | 80.7 |
| Post 230 mesh | 24 | 5.11E+08 | 840 | 36.36 | 67.19 | 91.48 | 73.8 |

Results indicate that recovery of oocysts and final pellet levels were similar for both diets. During the sieving process, it was noted qualitatively that the sample derived from the corn/soy+enzymes diet was less viscous and poured through the sieves more easily than the non-enzyme treatment samples.

Overall, the use of enzymes in the feed did not significantly reduce the volume of solids either upon collection or after sieving. However, a lessening of pasty vent problems was observed with the birds consuming the enzyme-containing diet, which is likely attributable to the viscosity-lowering effect of enzymes. While enzymes in the feed were not successful in reducing the amount of starting solids, the inclusion of enzymes in the diet during oocyst production can provide ancillary benefits such as improved general bird health and improved sieving characteristics.

Materials produced using the corn/soy diet with or without enzymes as well as a barley/soy diet with enzymes were further tested using downstream processing either with or without enzymes followed by flotation using two different flotation solutions.

Flotation Only.

A 3 L sample of sieved material was pelleted by centrifuging at 3000 rpm for 10 min. The supernatant was decanted and the pellet volume estimated. Three volumes of flotation solution (either magnesium sulfate or glycerol-arginine) were used to resuspend the pellet. The sample was centrifuged at 3000 rpm for 10 min to float the oocysts. The entire supernatant including the floated oocysts was decanted into another container and diluted with 4 volumes of water. The sample was centrifuged at 3000 rpm for 10 min to pellet the oocysts. The supernatant was decanted and discarded. The oocyst pellet was resuspended in 200 mL 5% citric acid.

Enzyme Treatment Followed by Flotation.

A 3 L sample of sieved material was pelleted by centrifuging at 3000 rpm for 10 min. The supernatant was decanted and the pellet volume estimated. Two volumes of water were used to resuspend the pellet. Potassium phosphate dibasic was added to adjust the pH to 5.0. Cellulase was added to 20%, and pectinase was added to 4%. The sample was incubated at room temperature and stirred for about 4 hours. The sample was centrifuged at 3000 rpm for 10 min. The supernatant was decanted and the pellet volume estimated. The pellet was resuspended using 3 volumes of flotation solution (either magnesium sulfate or glycerol-arginine). The sample was centrifuged at 3000 rpm for 10 min to float the oocysts. The entire supernatant including the floated oocysts was transferred into another container and diluted with 4 volumes of water. The diluted sample was centrifuged at 3000 rpm for 10 min to pellet the oocysts. The supernatant was discarded and the oocyst pellet was resuspended in 200 mL 5% citric acid.

TABLE 14

Purification of Oocysts: Effects of Diet, In-Process Enzyme Treatment, and Flotation Solution Composition on Debris Removal and Oocyst Recovery.

| Diet | Cellulase-Pectinase treatment | Flotation solution | Percent debris reduction | Percent oocyst recovery |
|---|---|---|---|---|
| Corn + soy | No | Magnesium sulfate | 64 | 76 |
|  | Yes | Magnesium sulfate | 84 | 88 |
|  | No | Glycerol-arginine | 65 | 84 |
|  | Yes | Glycerol-arginine | 96 | 57 |
| Corn + soy + enzymes | No | Magnesium sulfate | 60 | 77 |
|  | Yes | Magnesium sulfate | 92 | 60 |
|  | No | Glycerol-arginine | 70 | 78 |
|  | Yes | Glycerol-arginine | 98 | 44 |
| Barley + soy + enzymes | No | Magnesium sulfate | 77 | 99 |
|  | Yes | Magnesium sulfate | 86 | 82 |
|  | No | Glycerol-arginine | 75 | 97 |
|  | Yes | Glycerol-arginine | 96 | 90 |

In-process treatment with enzymes followed by flotation using glycerol-arginine yielded better debris removal compared to other treatments.

Generally, oocyst recovery was improved using the barley-based diet.

EXAMPLE 7

Viability of Oocysts Produced Using Enzymes

The effect of using enzymes either in the feed or in processing on *E. maxima* oocyst viability was tested. *E. maxima* oocysts were produced in broilers either with or without enzymes in the feed. Oocysts produced using either feed were then purified with or without enzymes in the purification process.

To test viability of the purified oocysts produced as described above, five broilers were placed per pen with five pens per treatment in battery cages. Birds were fed normal broiler starter feed throughout the study. Birds were administered 1000 sporulated *E. maxima* oocysts of the appropriate treatment via oral gavage. Oocysts were less than two months old at the time of administration. Papers were pulled and 2 L collection fluid (10% citric acid and 0.25% propionic acid) were added to each pan on D5 post-challenge. On D8 post challenge, birds were euthanized, and feces were collected from each pan individually. Each sample was adjusted to 4 L total volume with water, blended briefly at medium speed in a commercial blender, and subsampled.

Oocyst concentrations were determined using the McMasters method. Results were as indicated in the following table:

TABLE 15

Comparison of Oocyst Output Resulting from Oocysts Produced and/or Processed using Enzymes.

| Treatment # | Enzymes used in Diet during oocyst production | Enzymes used in processing | Total oocysts per bird | CV (%) |
|---|---|---|---|---|
| 1 | No | No | 3.88E+07 | 11.0 |
| 2 | No | Yes | 3.98E+07 | 14.5 |
| 3 | Yes | No | 3.70E+07 | 8.7 |
| 4 | Yes | Yes | 3.62E+07 | 5.4 |

Conclusion.

The use of enzymes either in the diet or in processing or both has no effect on oocyst viability as determined by oocyst output.

EXAMPLE 8

Production Scale Use of Enzymes for Oocyst Purification Methods

Chickens were infected with *Eimeria*, and the resulting oocyst-rich feces were collected into a solution of 10% citric acid, 0.75% hydrogen peroxide, and 0.25% propionic acid during the peak output period for each species. Feces were sieved to remove large particles, and oocysts were sporulated. The suspension was centrifuged to pellet the oocysts, and the oocyst-free supernatant was discarded. The pelleted material containing the oocysts was resuspended in phosphate buffer at pH ~5. Cellulase and pectinase enzymes were added at approximately 5 to 10% each on a volume basis, and the suspension was stirred overnight at room temperature. Total oocysts and total solids were determined before and after enzyme treatment.

Results.

Results are shown in the Table 16 below:

TABLE 16

Results of Production Scale Use of Enzymes in Oocyst Purification.

| Batch Number | Eimeria species | Oocyst Recovery (%) | Total solids prior to enzymatic digestion (L) | Total solids after enzymatic digestion (L) | Percent solids reduction |
|---|---|---|---|---|---|
| 1 | E. tenella | 93.3 | 14.39 | 5.58 | 61.2 |
| 2 | E. tenella | 85.3 | 12.10 | 4.29 | 64.5 |
| 3 | E. maxima | 125.3 | 21.13 | 9.75 | 53.9 |
| 4 | E. maxima | 100.0 | 15.90 | 5.18 | 67.4 |
| 5 | E. maxima | 106.0 | 12.50 | 6.48 | 48.2 |

Enzymatic digestion successfully reduced the volume of solids by an average of 59%. Oocyst recovery was essentially quantitative in each case.

Reducing the amount of solids to be processed has several positive effects on the process, including 1) reducing the amount of reagents needed for downstream processing, 2) reducing the scale of equipment needed for downstream processing, and 3) improving the efficiency of the subsequent purification steps.

Although the foregoing invention has been described in some detail by way of illustration and example for purposes of clarity and understanding, it will be apparent that certain changes and modifications may be practiced within the scope of the appended claims and equivalents thereof.

That which is claimed:

1. A method of purifying oocysts from a composition comprising fecal material, comprising contacting the composition with polysaccharidase under conditions sufficient to reduce the amount of fecal material in the composition.

2. The method according to claim 1, further comprising removing the polysaccharidase from contact with the oocysts.

3. The method according to claim 2, further comprising collecting the oocysts following contact with the polysaccharidase.

4. The method according to claim 1, wherein the polysaccharidase comprises an enzyme selected from the group consisting of cellulase, pectinase, amylase, xylanase, arabinase, alpha-galactosidase, hemi-cellulase, beta-glucanase, beta-glucosidase, amyloglucosidase, and any combination thereof.

5. The method according to claim 4, wherein the polysaccharidase comprises cellulase.

6. The method according to claim 5, wherein the polysaccharidase comprises cellulase and pectinase.

7. The method according to claim 5, wherein cellulase is present in an amount in the range of $2 \times 10^4$ to $50 \times 10^4$ units/liter.

8. The method according to claim 5, wherein cellulase is present in an amount in the range of $4 \times 10^4$ to $25 \times 10^4$ units/liter.

9. The method according to claim 1, wherein the method comprises:
contacting the composition with polysaccharidase comprising cellulase and pectinase, and then
contacting the composition with polysaccharidase comprising amylase.

10. The method according to claim 1, wherein the oocysts are sporulated oocysts.

11. The method according to claim 1, wherein the oocysts are *Eimeria* oocysts.

12. The method according to claim 11, wherein the *Eimeria* oocysts are selected from the group consisting of *E. maxima* oocysts, *E. mitis* oocysts, *E. tenella* oocysts, *E. acervulina* oocysts, *E. brunetti* oocysts, *E. necatrix* oocysts, *E. praecox* oocysts, *E. mivati* oocysts, and any combination thereof.

13. The method according to claim 11, wherein the *Eimeria* oocysts are selected from the group consisting of *E. meleagrimitis* oocysts, *E. adenoeides* oocysts, *E. gallopavonis* oocysts, *E. dispersa* oocysts, *E. innocua* oocysts, and *E. subrotunda* oocysts, and any combination thereof.

14. The method according to claim 11, wherein the *Eimeria* oocysts are selected from the group consisting of *E. zuernii* oocysts, *E. bovis* oocysts, and any combination thereof.

15. The method according to claim 11, wherein the *Eimeria* oocysts are selected from the group consisting of *E. ahsata* oocysts, *E. bakuensis* oocysts, *E. crandallis* oocysts, *E. faurei* oocysts, *E. granulosa* oocysts, *E. intricata* oocysts, *E. marsica* oocysts, *E. ovinoidalis* oocysts, *E. pallida* oocysts, *E. parva* oocysts, *E. weybridgensis* oocysts, and any combination thereof.

16. The method according to claim 11, wherein the *Eimeria* oocysts are selected from the group consisting of *E. intestinalis* oocysts, *E. vejdovskyi* oocysts, *E. piriformis* oocysts, *E. coecicola* oocysts, *E. irresidua* oocysts, *E. fla-*

*vescens* oocysts, *E. exigua* oocysts, *E. magna* oocysts, *E. perforans* oocysts, *E. media* oocysts, *E. stiedai* oocysts, and any combination thereof.

17. The method according to claim 1, wherein the composition is contacted with polysaccharidase for 30 minutes to 24 hours.

18. The method according to claim 15, wherein the composition is contacted with polysaccharidase for two hours to ten hours.

19. The method according to claim 1, wherein the composition is contacted with polysaccharidase at a temperature in the range of 15° C. to 30° C.

20. The method according to claim 19, wherein the composition is contacted with polysaccharidase at a temperature in the range of 21° C. to 27° C.

21. The method according to claim 1, wherein the composition is contacted with polysaccharidase at a pH in the range of pH 1 to pH 7.5.

22. The method according to claim 21, wherein the composition is contacted with polysaccharidase at a pH in the range of pH 4 to pH 6.

23. The method according to claim 1, wherein the method comprises two enzyme digestion steps, which are carried out at different pH.

24. The method according to claim 23, the method comprising:
 contacting the composition with polysaccharidase comprising cellulase and amylase at a pH in the range of pH 4 to pH 5.5, and then contacting the composition with polysaccharidase comprising amylase at a pH in the range of 4 to pH 7.5.

25. The method according to claim 1, wherein the method further comprises a density flotation process.

26. The method according to claim 25, wherein the density flotation process is carried out after contacting the composition with polysaccharidase.

27. The method according to claim 25, wherein the density flotation solution is a salt solution.

28. The method according to claim 25, wherein the salt solution is a magnesium sulfate solution.

29. The method according to claim 25, wherein the density flotation solution is a glycerol solution.

30. The method according to claim 29, wherein the glycerol solution is a glycerol-polyarginine solution.

31. The method according to claim 1, wherein the fecal material has been collected from an animal that has been fed a diet having a large mean particle size prior to the collection period.

32. The method according to claim 31, wherein the large particle diet comprises barley.

33. The method according to claim 32, wherein the large particle diet comprises barley-soy.

34. A method of purifying *Eimeria* oocysts from a composition comprising fecal material, comprising contacting the composition with polysaccharidase comprising cellulase under conditions sufficient to reduce the amount of fecal material in the composition.

35. The method according to claim 34, further comprising removing the polysaccharidase from contact with the oocysts.

36. The method according to claim 35, further comprising collecting the oocysts following contact with the polysaccharidase.

37. The method according to claim 34, wherein the polysaccharidase further comprises pectinase.

38. A method of purifying *Eimeria* oocysts from a composition comprising fecal material, comprising contacting the composition with polysaccharidase consisting of cellulase and pectinase under conditions sufficient to reduce the amount of fecal material in the composition.

* * * * *